(12) United States Patent
Suchocki

(10) Patent No.: US 10,330,343 B2
(45) Date of Patent: Jun. 25, 2019

(54) DEVICES FOR CONTROL OF CONDENSATION AND METHODS OF USE THEREOF

(71) Applicant: T2 Biosystems, Inc., Lexington, MA (US)

(72) Inventor: Adam Suchocki, Lexington, MA (US)

(73) Assignee: T2 Biosystems, Inc., Lexington, MA (US)

( * ) Notice: Subject to any disclaimer, the term of this patent is extended or adjusted under 35 U.S.C. 154(b) by 680 days.

(21) Appl. No.: 14/378,257

(22) PCT Filed: Feb. 21, 2013

(86) PCT No.: PCT/US2013/027050
§ 371 (c)(1),
(2) Date: Aug. 12, 2014

(87) PCT Pub. No.: WO2013/126518
PCT Pub. Date: Aug. 29, 2013

(65) Prior Publication Data
US 2015/0010295 A1 Jan. 8, 2015

Related U.S. Application Data

(60) Provisional application No. 61/601,844, filed on Feb. 22, 2012.

(51) Int. Cl.
| B01L 7/00 | (2006.01) |
| F27D 11/00 | (2006.01) |
| H05B 3/06 | (2006.01) |
| F24H 9/02 | (2006.01) |
| B01L 7/02 | (2006.01) |
| H05B 3/00 | (2006.01) |
(Continued)

(52) U.S. Cl.
CPC ............... *F24H 9/02* (2013.01); *B01L 7/02* (2013.01); *H05B 3/00* (2013.01); *B01L 3/5082* (2013.01); *B01L 3/50851* (2013.01); *B01L 7/52* (2013.01); *B01L 2300/0829* (2013.01); *B01L 2300/1827* (2013.01); *B01L 2300/1883* (2013.01); *G01N 2035/00356* (2013.01)

(58) Field of Classification Search
CPC .................................. H05B 3/00; F24H 9/02
USPC ................. 392/411, 451, 444, 449; 219/494
See application file for complete search history.

(56) References Cited

U.S. PATENT DOCUMENTS 2,806,123 A * 9/1957 Steinbock, Jr. ........... A61L 2/26
126/20
3,002,895 A * 10/1961 Freedman ........... B01F 11/0014
435/303.3
(Continued)

OTHER PUBLICATIONS

Lifesign, Model Culture M Incubator, digest # 05866, 2009.*
(Continued)

*Primary Examiner* — Dana Ross
*Assistant Examiner* — Lawrence H Samuels
(74) *Attorney, Agent, or Firm* — Clark & Elbing LLP; Karen L. Elbing

(57) ABSTRACT

The present invention relates to devices including a heating element with an opening, which can control condensation of liquid samples during thermal incubation. The opening of the heating element can provide direct access to the samples in a process that may be automated. The invention also provides methods for heating containers.

26 Claims, 2 Drawing Sheets

Heated Ring Assembly

(51) Int. Cl.
*B01L 3/00* (2006.01)
*G01N 35/00* (2006.01)

(56) References Cited

U.S. PATENT DOCUMENTS

| | | | | | |
|---|---|---|---|---|---|
| 3,210,996 | A | * | 10/1965 | Harwood | G01K 1/14 219/209 |
| 3,601,372 | A | * | 8/1971 | Harmes | B01F 11/0014 137/579 |
| 3,634,651 | A | * | 1/1972 | Siegel | B01L 7/00 219/386 |
| 3,661,117 | A | * | 5/1972 | Cornelius | C23C 14/04 118/715 |
| 4,747,693 | A | * | 5/1988 | Kahl | B01F 11/0008 211/74 |
| 5,041,719 | A | * | 8/1991 | Harris | C23C 14/243 118/725 |
| 5,052,812 | A | * | 10/1991 | Tannenbaum | B01F 11/0014 366/145 |
| 5,061,448 | A | * | 10/1991 | Mahe | B01L 7/02 219/400 |
| 5,577,837 | A | * | 11/1996 | Martin | B01F 11/0068 366/145 |
| 5,819,842 | A | * | 10/1998 | Potter | B01L 7/54 165/206 |
| 6,469,285 | B2 | * | 10/2002 | Inami | B01L 7/00 126/340 |
| 6,518,060 | B2 | * | 2/2003 | Heimberg | B01L 3/50853 220/526 |
| 6,730,883 | B2 | * | 5/2004 | Brown | B01L 3/50851 219/385 |
| 6,770,482 | B1 | * | 8/2004 | Flanagan | B01J 19/0046 422/130 |
| 7,459,302 | B2 | * | 12/2008 | Reid | B01L 7/52 165/206 |
| 7,695,688 | B2 | * | 4/2010 | Reed | G01N 35/028 422/552 |
| 7,765,918 | B2 | * | 8/2010 | Garniss | A21B 1/48 126/20 |
| 8,409,807 | B2 | | 4/2013 | Neely et al. | |
| 8,563,298 | B2 | | 10/2013 | Lowery, Jr. et al. | |
| 8,883,423 | B2 | | 11/2014 | Neely | |
| 9,046,493 | B2 | | 6/2015 | Neely et al. | |
| 2002/0100582 | A1 | * | 8/2002 | Oldenburg | B01F 11/0258 165/253 |
| 2002/0182117 | A1 | * | 12/2002 | Coassin | B01J 19/0046 422/400 |
| 2003/0106682 | A1 | * | 6/2003 | Reid | B01L 7/52 165/206 |
| 2004/0053318 | A1 | * | 3/2004 | McWilliams | B01L 7/52 435/6.14 |
| 2004/0065655 | A1 | * | 4/2004 | Brown | B01L 3/50851 219/428 |
| 2004/0258568 | A1 | * | 12/2004 | Lurz | B01L 3/50851 422/552 |
| 2005/0233363 | A1 | * | 10/2005 | Harding | B01L 3/50851 435/6.16 |
| 2005/0255586 | A1 | * | 11/2005 | Shin | B01L 7/52 435/303.1 |
| 2006/0013736 | A1 | * | 1/2006 | Blok | B01L 3/50255 422/400 |
| 2006/0257127 | A1 | * | 11/2006 | Patterson | F24H 9/2021 392/441 |
| 2007/0105214 | A1 | * | 5/2007 | Micklash, II | C12M 45/02 435/306.1 |
| 2009/0120104 | A1 | * | 5/2009 | Federer | B01L 7/52 62/3.2 |
| 2009/0220385 | A1 | * | 9/2009 | Brown | B01F 13/1055 422/400 |
| 2010/0196212 | A1 | * | 8/2010 | Reed | B01L 3/5025 422/504 |
| 2010/0303690 | A1 | * | 12/2010 | Howell | B01L 3/50851 422/600 |
| 2011/0002699 | A1 | * | 1/2011 | Aoki | G03G 15/238 399/17 |
| 2011/0003699 | A1 | | 1/2011 | Yoder et al. | |
| 2011/0239673 | A1 | * | 10/2011 | Junge | F28D 20/02 62/238.7 |
| 2012/0301888 | A1 | | 11/2012 | Neely et al. | |
| 2013/0029345 | A1 | | 1/2013 | Neely et al. | |
| 2013/0048623 | A1 | * | 2/2013 | Jamison | G01N 25/00 219/389 |
| 2013/0244238 | A1 | | 9/2013 | Neely et al. | |
| 2013/0260367 | A1 | | 10/2013 | Lowery, Jr. et al. | |
| 2013/0273522 | A1 | | 10/2013 | Lowery, Jr. et al. | |
| 2013/0273523 | A1 | | 10/2013 | Neely et al. | |
| 2013/0343734 | A1 | * | 12/2013 | Dock, II | B28B 11/245 392/441 |
| 2014/0106442 | A1 | | 4/2014 | Lowery, Jr. et al. | |
| 2014/0120523 | A1 | | 5/2014 | Lowery, Jr. et al. | |

OTHER PUBLICATIONS

International Preliminary Report on Patentability for International Application No. PCT/US2013/027050, dated May 12, 2015 (5 pages).

International Search Report and Written Opinion for International Application No. PCT/US13/27050, dated May 3, 2013 (12 pages).

* cited by examiner

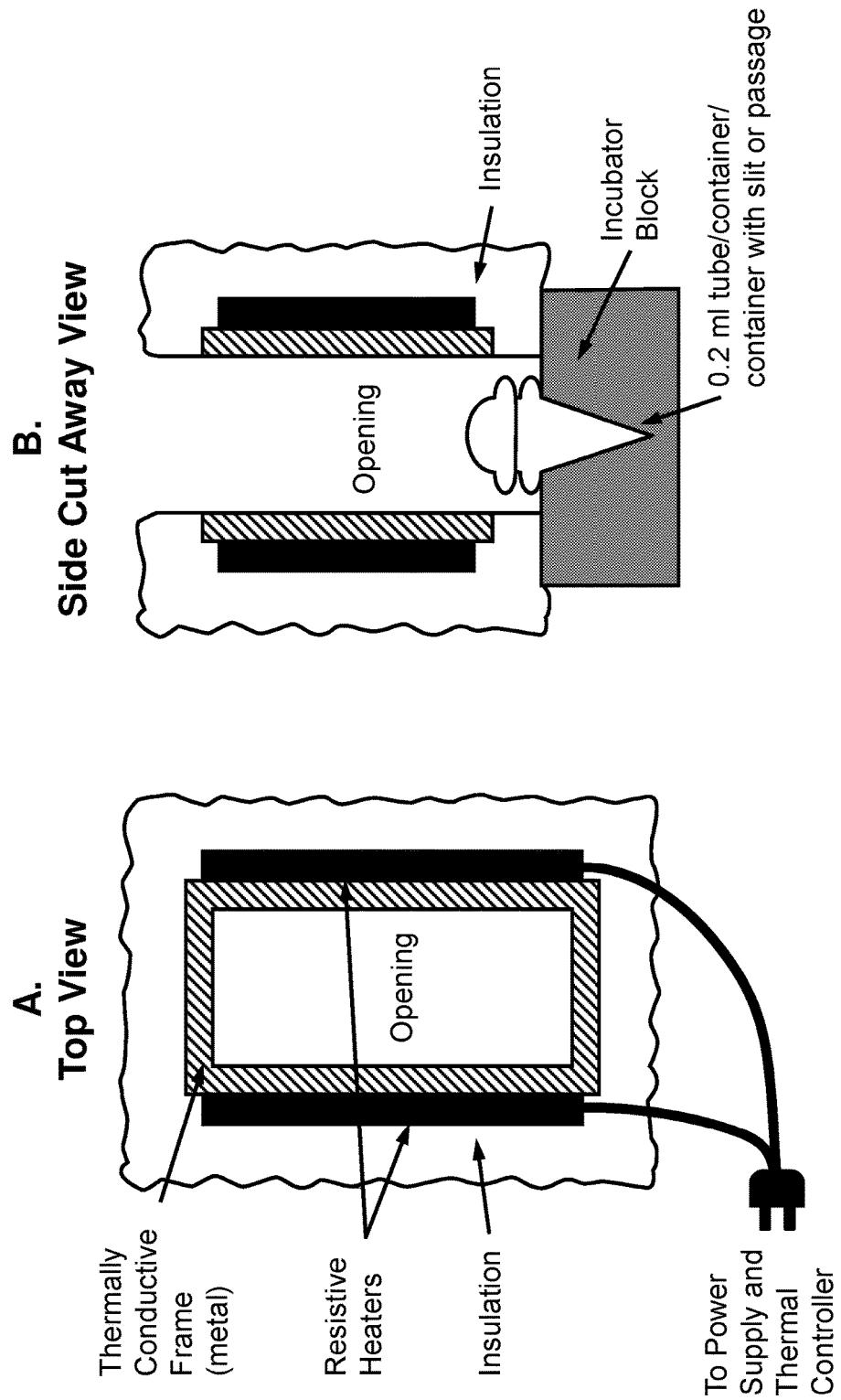
Figure 1. Heated Ring Assembly

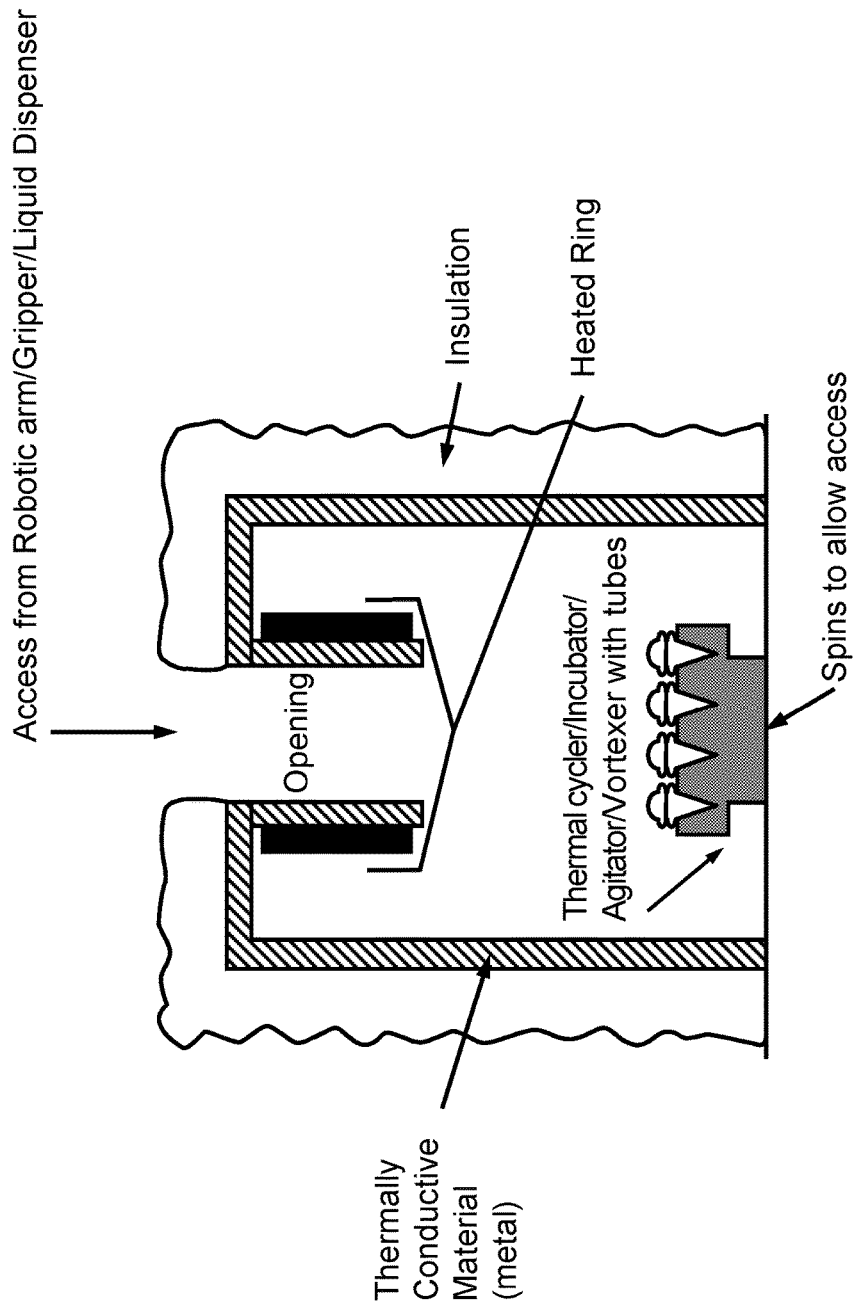
Figure 2. Heated Ring with Shroud over Vortexer

DEVICES FOR CONTROL OF CONDENSATION AND METHODS OF USE THEREOF

CROSS-REFERENCE TO RELATED APPLICATIONS

This application is a national phase of International Application No. PCT/US2013/027050, filed Feb. 21, 2013, which claims the benefit of U.S. Provisional Application No. 61/601,844, filed Feb. 22, 2012, which is hereby incorporated by reference in its entirety.

BACKGROUND OF THE INVENTION

Devices for incubating a liquid sample at uniform temperatures above or below ambient temperature are commonly required during the processing steps and procedures of different standard assays. A thermal incubation device typically includes an element that heats or cools the bottom and sides of a container holding the liquid sample, thereby bringing the sample to its desired incubation temperature. The top of the container is often unable to achieve the desired incubation temperature because it is not in direct contact with the heating or cooling element. The unwanted temperature gradient may lead to significant amounts of condensation collecting at the top of the sample container. The condensation in the sample container may result in an unwanted reduction in the sample volume. In a standard assay, a reduction in sample volume can lead to altered reaction conditions, which may negatively influence the assay results.

Approaches for minimizing condensation during sample incubation at a temperature above or below ambient temperature are known in the art. Thermal cycling devices, which often incubate liquid samples at elevated temperatures, may additionally include a heated cover that directly contacts the closed top of the reaction tube and heats the top to a temperature equivalent to or hotter than the sides of the tube. Alternatively, the liquid sample may be overlaid with mineral oil or a similar reagent to create a physical vapor barrier during the incubation.

The above approaches, however, have limitations that generally prevent them from being completely effective. An element such as a heated cover prevents facile access to the sample during the incubation process. The use of mineral oil may not be compatible with the assay conditions and also makes access to the sample cumbersome. Both solutions severely limit the ability of the incubation process to be efficiently automated.

It is therefore important to develop an alternative means of minimizing condensation of samples during the incubation process. Accordingly, there is an unmet need in the field for a device that provides an effective solution to the problem of sample condensation during thermal incubation, while not suffering from the limitations of the prior art.

SUMMARY OF THE INVENTION

The present invention relates to a device including a heating element that minimizes condensation of liquid samples during thermal incubation. In a first aspect, the invention features a device for heating a liquid sample, which includes a heating element positioned above a frame having at least one well for holding a liquid sample, where the heating element includes an opening above the well and is positioned to heat the opening. In one embodiment, the cross-section area of the opening is equal to, or larger than, the cross-section area of the well. In another embodiment, the heating element heats the opening to a temperature greater than the temperature of the well. Typically, the heating element heats the opening to a temperature 5, 10, 20, 30, 40, 50, 75, or 100 degrees centigrade (° C.) greater than the temperature of the well.

In other embodiments, the opening of the heating element has a depth of between 5 millimeters (mm) and 200 mm (e.g., between 5 mm to 50 mm, 50 mm to 100 mm, 100 mm to 150 mm, or 150 mm to 200 mm). The cross-section of the opening may be substantially rectangular, circular, or substantially oval. In some embodiments, the heating element has a rectangular opening with a first dimension of between 5 mm and 200 mm (e.g., between 5 mm to 50 mm, 50 mm to 100 mm, 100 mm to 150 mm, or 150 mm to 200 mm) and a second dimension of between 5 mm and 200 mm (e.g., between 5 mm to 50 mm, 50 mm to 100 mm, 100 mm to 150 mm, or 150 mm to 200 mm). In a particular embodiment, the heating element has a rectangular opening with a depth of about 25 mm, and a cross-section with a first dimension of about 10 mm and a second dimension of about 50 mm.

In any of the above embodiments, the frame of the device may comprise multiple wells. In a preferred embodiment, the opening of the heating element is positioned above the multiple wells. In one embodiment, the frame is a thermal cycler, vortexer, incubator, or agitator. In another embodiment, the device further includes a second heating element positioned below or about the frame. In yet another embodiment, the heating element is a resistive heating element. In yet another embodiment, the condensation control device (heating element positioned above frame) further includes a robotic arm. In some embodiments, the robotic arm includes a gripper and a liquid dispenser. In some embodiments, the opening of the heating element is sufficiently large to allow passage of the gripper and/or liquid dispenser. In other embodiments, the gripper and/or liquid dispenser are automated.

In another aspect, the invention features a method of heating a liquid sample, which includes inserting the liquid sample into a well of any of the devices above, heating the liquid sample, and heating the opening.

In another aspect, the invention features a method of heating a liquid sample, which includes providing the liquid sample in a container including a top surface and providing a heating element above the container, wherein the heating element has an opening positioned above the container and the container top is within the opening, and whereby the heating element heats the top surface of the container. In one embodiment, the heating of the top surface of the container is sufficient to prevent condensation of liquid on the top surface. In another embodiment, the method further includes providing a second heating element positioned below or about the container. In another embodiment, the top of the container contains a slit or a passage. In another embodiment, the method includes further providing a liquid dispenser. In yet another embodiment, the liquid dispenser dispenses liquid through the top of the container while the container is positioned below the opening. In other embodiments, the method further includes providing a gripper, passing the gripper through the opening, gripping the top of the container with the gripper, and passing the container through the opening using the gripper. In other embodiments, the liquid dispenser and gripper are automated. In some embodiments, the heating element heats the opening to a temperature greater than the temperature of the liquid sample. In a preferred embodiment, the heating element heats the opening to a temperature 10, 20, 30, 40, 50, 75, or 100 degrees centigrade greater than the temperature of the liquid sample.

In another aspect, the invention features a device for heating a liquid sample, which includes a frame including a well for holding the liquid sample, wherein the frame is on an agitation device and both frame and agitation device are within an enclosure, a first heating element positioned above the frame, wherein the first heating element includes an opening above the well and is positioned to heat the opening, and a second heating element positioned below or about the frame.

In yet another aspect, the invention features a method of heating a liquid sample, which includes providing the liquid sample in a container including a top surface and providing a heating element above the container, wherein the heating element has an opening positioned above the container and the container top is proximate to the opening, and whereby the heating element heats the top surface of the container.

Definitions

By "container" is meant a rigid shaped article with a top, bottom, and sides, wherein the top optionally contains an opening for access to an interior that is able to contain liquid, gaseous, and/or solid samples. It is not limited to any particular shape, and may, for example, have a cross-section with a square, rectangular, triangular, circular, or oval shape. In some embodiments, the container may have an openable top surface, for example, a lid, cover, or cap.

The term "gripper" as used herein refers to a device (e.g., a robotic device) for prehension or otherwise for handling of an object or material. Non-limiting examples of grippers include impactive grippers, which include jaws or claws that physically grasp the object, and astrictive grippers, which apply suction forces to the surface of the object for handling. Typically, the object is a container.

By "opening" in the context of a surrounding heating device is meant the space immediately bounded by the interior surfaces of the thermally conductive material of the heating device and open on both sides of the heating device (e.g., above and below the opening if the opening is in a horizontal orientation). The opening allows, e.g., a robotic arm or other object to pass through and access a sample positioned beneath the heating device.

The term "well" as used herein includes any recess, indentation, or holding space in which a sample can be placed and/or stored. Typically, a well holds a container with a liquid sample. A well may also directly contain the liquid sample. A well is not limited to any particular shape, and may, for example, have a cross-section with a square, rectangular, triangular, circular, or oval shape. In some embodiments, the well is provided in a frame.

Other features and advantages of the invention will be apparent from the following Detailed Description, the drawings, and the claims.

BRIEF DESCRIPTION OF THE DRAWINGS

FIG. 1A is a schematic top perspective view of one example of a heating element according to the present invention.

FIG. 1B is a schematic cross-sectional side perspective view of the heating element in FIG. 1A and an incubator block frame with sample container, showing the relative position of each.

FIG. 2 is a schematic cross-sectional view of one example of a heating element according to the present invention and a vortexer frame, showing the relative position of each.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION OF THE INVENTION

The present invention is based, at least in part, on a heating element that can minimize condensation of a liquid sample during thermal incubation and provide easy access to the sample via an opening. The heating element may be used with a thermal incubation frame (e.g., an incubator, thermal cycler, vortexer, or agitator) as described below to form, for example, a condensation control device. The heating element may be particularly useful in automated devices for which direct access to samples during thermal incubation is required.

Heating Element with Opening

The present invention provides a heating element that can, for example, minimize or prevent condensation of a liquid sample in a thermal incubation frame (e.g., an incubator, thermal cycler, vortexer, or agitator). The heating element includes an opening that is positioned directly above the frame and heats the area contained in and, for example, immediately below the opening, thereby heating the exposed top of a container in the frame and, for example, controlling condensation. The heating element can control condensation while allowing continuous access to the sample in the thermal incubation frame (e.g., by automated tools such as a robotic arm).

In some embodiments, the heating element is a resistive heating element. As depicted in FIG. 1A, the heating element can include a thermally conductive metal frame (1) with an opening (2), upon which two resistive heaters (3) are applied. The thermally conductive metal may be a metal such as silver (Ag), bismuth (Bi), gallium (Ga), indium (In), tin (Sn), lead (Pb), or an alloy thereof, which may further include aluminum (Al), gold (Au), cadmium (Cd), copper (Cu), nickel (Ni), antimony (Sb), zinc (Zn), or a combination thereof. Thermally conductive metals are known in the art and are commercially available (see, e.g., U.S. Pat. Pub. No. 2010/0208432). One skilled in the art would be familiar with many types of resistive heaters (3) available or designable for heating a thermally conductive metal frame (1), and that these are encompassed within the scope of the invention.

As depicted in FIG. 1A, the resistive heaters (3) can be electrically connected to a controllable power source (5) for applying a current across the element. Control of the power source may be carried out by an appropriately programmed processor device (e.g., a computer), which receives signals from a temperature sensor in communication with the heating element. A wide variety of microsensors are available for determining temperatures, including thermocouples having a bimetallic junction which produces a temperature-dependent electromotive force (EMF), resistance thermometers which include material having an electrical resistance proportional to the temperature of the material, thermistors, IC temperature sensors, and quartz thermometers. (See, e.g., Horowitz and Hill, *The Art of Electronics*, Cambridge University Press, 1994). The temperature measured by the temperature sensor and the input for the power source can be interfaced with a processor which is programmed to receive and record this data, e.g., via an analog-digital/digital-analog (AD/DA) converter. The same processor will typically include programming for directing the delivery of appropriate current from the power source (5) to the resistive heaters (3) of the heating element for raising or lowering the temperature. The thermally conductive metal frame (1) and resistive heaters (3) can be covered by an insulation layer (4), which does not occlude the heated opening (2). The insulation layer (4) helps to maintain the temperature differential between the air contained within the heating element and external to the heating element of the invention. In another embodiment, the heating of the opening (2) is unregulated.

The opening (2) of the heating element may vary in size and shape. In one embodiment, the cross-section of the opening may be equal to, or larger than, the cross-section area of the sample well of the thermal incubation frame (6). The opening (2) typically has a depth of between 1 millimeters (mm) and 200 mm (e.g., between 5 mm to 50 mm, 50 mm to 100 mm, 100 mm to 150 mm, or 150 mm to 200 mm). The cross-section of the opening (2) may be, for example, substantially rectangular, circular, or oval. In an embodiment in which the opening (2) is substantially rectangular, the cross-section can have a first dimension of between 5 mm and 200 mm (e.g., between 5 mm to 50 mm, 50 mm to 100 mm, 100 mm to 150 mm, or 150 mm to 200 mm) and a second dimension of between 5 mm and 200 mm (e.g., between 5 mm to 50 mm, 50 mm to 100 mm, 100 mm to 150 mm, or 150 mm to 200 mm). In another embodiment, the opening (2) has a depth of about 25 mm and a substantially rectangular cross-section in which the first dimension is about 10 mm and the second dimension is about 50 mm.

In other embodiments, the heating element is positioned above a thermal incubation frame (6) that includes multiple wells (e.g., 2, 3, 4, 5, 6, 7, 8, 9, 10, 12, 16, 20, 24, 30, 36, 40, 48, 50, 60, 70, 72, 80, 84, 90, 96, 100, 125, 150, 175, 200, 300, 400, 500, or more wells) for multiple containers (7) of liquid samples (e.g., 2, 3, 4, 5, 6, 7, 8, 9, 10, 12, 16, 20, 24, 30, 36, 40, 48, 50, 60, 70, 72, 80, 84, 90, 96, 100, 125, 150, 175, 200, 300, 400, 500, or more containers of liquid samples). Preferably, the opening (2) of the heating element is positioned above the multiple wells of the frame (6). Similar to the case of a thermal incubation frame (6) containing a single well with a single sample, the heating element of the invention, for example, heats the multiple exposed tops of the containers (7) of liquid samples to control condensation.

In other embodiments, the heating element of the invention heats the area contained within and below the heated opening (2) to a temperature 5, 10, 20, 30, 40, 50, 75, or 100° C. greater than the temperature of the one or more wells of the frame (6). The superheated air can warm the tops of the one or more sample containers (7) and prevents condensation. The opening (2) may heat the tops of the one or more containers (7) to a high enough temperature that condensation can be evaporated back off of the tops of the one or more containers (7). Preferably, the opening (2) is heated to a high enough temperature that the equilibrium temperature of the air within the opening (2) and around the one or more containers (7) is at the desired temperature necessary to limit condensation despite the exchange of warm air with the environment through the open top of the opening (2).

Heating Element Applications

The heating element of the invention can be used to minimize or prevent condensation of a liquid sample in any thermal incubation frame (e.g., an incubator, thermal cycler, vortexer, or agitator).

Thermal Cycler with Heating Element

Methods for thermal cycling of DNA samples are known in the art. By performing the method of polymerase chain reaction (PCR), a single or few copies of a target DNA region can be amplified to several hundred thousand or more copies. PCR achieves this feat by repeating DNA synthesis reactions using a DNA polymerase and two kinds of primers, which hybridize to the target DNA template to create a primer-template junction upon which the DNA polymerase acts. The DNA region interposed between the primers is subsequently amplified following iterative rounds of denaturation of the target DNA template, annealing of primers to the target DNA template, and synthesis of a new strand of the target DNA by the DNA polymerase following extension from the newly generated primer-template junction. The amplification of the target DNA region permits its detection and use in standard molecular biological cloning and diagnostic techniques.

Typically, a thermal cycler is used to perform the PCR steps of template DNA denaturation, primer annealing, and DNA strand extension. A reaction mixture including the target DNA for amplification, DNA polymerase, primers, deoxynucleotide triphosphates (dNTPs), and salts (e.g., divalent cations, e.g., $Mg^{2+}$) is provided in a sample container, and the container is placed in a well on a thermal incubation frame (e.g., a thermal/heat block). The typical thermal cycler may provide multiple sample wells on the frame for multiple independent PCR amplifications to be synchronously performed. The thermal cycler can raise the temperature of the reaction mixture(s) to, for example, 94-98° C. to denature the template DNA, can lower the temperature to, for example, 50-65° C. to allow for annealing of the primers, can raise the temperature to, for example, 70-80° C. to allow for polymerase-dependent DNA strand extension, and can repeat the cycle, thereby amplifying the target DNA region. Since the steps of PCR are performed across a range of high temperatures, the liquid reagents of the reaction mixture condense and/or evaporate, which may influence the results of the PCR.

As shown in FIG. 1B, the heating element of the invention may be positioned above a thermal incubation frame (6) such as a thermal cycler. The heated opening (2) is able to prevent condensation and allow PCR to be performed without the requirement of a heated cover or addition of mineral oil. The opening (2) of the heating element allows direct access to the one or more tubes during the thermal cycling reaction. These features of the invention allow for the thermal cycler with the heating element to function as an automated device. In some embodiments, the cross-section of the opening (2) of the heating element is large enough to allow a robotic arm to pass through and access the one or more sample containers (7) of the thermal cycler frame (6). In particular embodiments, the robotic arm may include a gripper, a liquid dispenser, or both. In some embodiments, the liquid dispenser may access and dispense liquid (e.g., a reagent that promotes the PCR process) into the one or more sample containers (7) by a slit or a passage in the container (7) while the container (7) is below the opening (2) of the heating element (e.g., in a well of the frame). In other embodiments, the gripper may grip the top of a sample container (7) and pass the container (7) through the opening (2) or move the container (7) to another location on the frame (6). Typically, the liquid dispenser and gripper are automated. A fully automated thermal cycling device (e.g., a PCR machine) enables high-throughput assays to be performed, reduces sample preparation time, and minimizes errors or contamination introduced by a human (e.g., PCR product contamination effects, e.g., amplicon amplification).

The heating element can be used with a standard incubator in the same manner that it is used with a thermal cycler as described above.

Vortexer or Agitator with Heating Element

Numerous standard assays or protocols require that a sample is agitated or vortexed during an incubation step at a temperature above or below ambient temperature. Typically, containers with sealed tops are used to hold liquid samples in an agitator or vortexer. The samples can be placed within a completely enclosed incubation unit that maintains the desired incubation temperature while providing space for movement of the agitator or vortexer frame. These devices can prevent easy access to the samples during the agitation or vortexing process.

The heating element of the invention may be used with a vortexer or agitator positioned below a frame, which can hold one or more containers of liquid samples. As depicted in FIG. 2, the opening (2) of the heating element is positioned directly above the vortexer frame (9) and heats the area contained in and below the heated ring (8), thereby heating the exposed tops of the containers (7) of liquid samples in the frame (9) and controlling condensation. The heating element of the invention, when used with a movable thermal incubation frame (e.g., a frame positioned above a vortexer or agitator) (9), requires the addition of an insulated shroud that extends down from the heated opening (2) and encircles the entirety of the movable frame (9) to form the condensation control unit. The heating element enables samples in the vortexer frame (9) to be accessed through the heated opening (2) without resulting in an unwanted change in the temperature of the sample. Access to the samples through the heated opening (2) enables the vortexer device to be automated. An automated vortexer device using a heating element of the invention may include a robotic arm for manipulation of the samples as described above.

The heating element may be used with a standard agitator frame in a similar manner to its use with a vortexer as described above.

EXAMPLES

The following examples are provided for the purpose of illustrating the invention and are not meant to limit the invention in any way.

Example 1. Heated Opening

As depicted in FIG. 1A, the heating device of the invention includes a thermally conductive metal frame opening (2), to which resistive heaters (3) are applied that electrically connect the heated opening (2) to a controllable power source (5). The heating device further includes a layer of insulation (4) around the heated opening (2) to minimize thermal loss to the external environment. The opening (2) of the heating device may be any cross-sectional shape and is depicted in FIG. 1A as a rectangular opening (2). The opening (2) contains air, which can be heated by the heating device.

Example 2. Condensation Control Devices

The heating element of the invention may be positioned above a thermal incubation frame (6), such as a thermal cycler or an incubator block, as depicted in FIG. 1B. The frame (6) may include one or more wells to hold one or more containers (7) of samples. In FIG. 1B, the incubator frame (6) includes one well, which holds a 0.2-mL capped tube (7) with liquid sample. The opening (2) of the heating element is positioned above the well holding the sample. Condensation of the liquid sample on the top surface of the tube is prevented by the heated opening (2), which provides heated air to the top surface of the tube (7) at a temperature sufficient to prevent condensation (e.g., at a temperature greater than the temperature of the well of the frame) in the condensation control unit.

This principle can be applied in embodiments in which the thermal incubation frame is movable or positioned on or about a movable platform (e.g., an agitator or vortexer) (9). The ring-shaped heating element may be used to control sample condensation, as depicted in FIG. 2. The heated ring (8) is positioned above the movable frame (9) including one or more containers (7) of liquid samples. The entirety of the frame (9) and samples is enclosed within a shroud, which extends down from the heated opening (2) and is composed of, at least in part, a thermally conductive metal material (1) covered by a layer of insulation (4). The dimensions of the insulated enclosure are carefully controlled to allow for the creation of a condensation control unit in which the liquid samples are held at a desired temperature above ambient temperature and the heated opening (2) prevents unwanted condensation.

The devices of the invention provide direct access to the samples via the opening of the heating element. The samples may be manually accessed by a human or accessed remotely using an automated system. The automated devices of the present invention may include a robotic arm (e.g., a robotic arm with a gripper and/or liquid dispenser) to facilitate sample processing for a given assay. The devices of the invention are useful for the development of automated in vitro diagnostic (IVD) devices that rely on a robotic arm to manipulate sample tubes or as a component used in conjunction with lab automation platforms.

Example 3. Performance Data

A prototype ring 25 mm high with a 10 mm×50 mm opening was tested with a 100-μl sample of deionized $H_2O$ in Axygen 0.2-ml PCR tubes with domed caps. The block temperature (sample temperature) was set at 95° C. The results of this experiment are set forth in Table 1.

TABLE 1

| Ring Temperature | Condensation Observation |
| --- | --- |
| OFF | Cap completely filled with condensation >20% drop in volume |
| 95° C. | Large droplets of $H_2O$ in cap 10-20% drop in volume |
| 110° C. | Fog, small droplets in cap <10% drop in volume |
| 130° C. | No visible condensation in cap or drop in volume |

Other ring configurations (higher walls, wider opening) produced visible condensation free operation at different temperatures (120-135° C.). A 20% change in condensation did correlate to a 20% change in sample concentration, as measured with paramagnetic beads and NMR (T2).

Other Embodiments

All publications, patents, and patent applications mentioned in the above specification are hereby incorporated by reference. Various modifications and variations of the described method and system of the invention will be apparent to those skilled in the art without departing from the scope and spirit of the invention. Although the invention has been described in connection with specific embodiments, it should be understood that the invention as claimed should not be unduly limited to such specific embodiments. Indeed, various modifications of the described modes for carrying out the invention that are obvious to those skilled in the art are intended to be within the scope of the invention.

Other embodiments are in the claims.

What is claimed is:

1. A heating device, said device comprising:
    (a) a frame comprising at least one well for holding a liquid sample,
    (b) a heating element positioned above the frame, wherein the heating element does not contact the frame or the sample and is configured to heat the air above the sample, and
    (c) an opening positioned within the heating element and above the at least one well, wherein the opening has a lateral cross-section sized to permit passage of a gripper or liquid dispenser to the well; wherein the heating element is configured to heat the opening to a temperature greater than the temperature of the well; and wherein the opening is configured to allow, throughout the device's use, continuous access to the well by the gripper or liquid dispenser.

2. The device of claim 1, wherein the lateral cross-section of said opening is equal to, or larger than, the lateral cross-section area of said well.

3. The device of claim 1, wherein said heating element heats said opening to a temperature 5, 10, 20, 30, 40, 50, 75, or 100 degrees centigrade greater than the temperature of said well.

4. The device of claim 1, wherein said opening has a depth of between 5 millimeters (mm) and 200 mm.

5. The device of claim 2, wherein said lateral cross-section of said opening is substantially rectangular.

6. The device of claim 5, wherein said lateral cross-section has a first dimension of between 5 mm and 200 mm and has a second dimension of between 5 mm and 200 mm.

7. The device of claim 5, wherein said depth is between 5 mm and 50 mm, and said lateral cross-section has a first dimension between 5 mm and 50 mm and a second dimension between 5 mm and 50 mm.

8. The device of any of claim 2, wherein said lateral cross-section of said opening is circular or substantially oval.

9. The device of claim 1, wherein said device comprises multiple wells.

10. The device of claim 9, wherein said opening is positioned above said multiple wells.

11. The device of claim 1, wherein said frame is a thermal cycler, vortexer, incubator, or agitator.

12. The device of claim 11, wherein a second heating element is positioned below or about said frame.

13. The device of claim 12, wherein one or both of said heating elements is a resistive heating element.

14. The device of claim 1, wherein said heating element further comprising a robotic arm.

15. The device of claim 14, wherein said heating element further comprising a gripper and a liquid dispenser.

16. The device of claim 15, wherein said gripper and/or said liquid dispenser are automated.

17. A method of heating a liquid sample, said method comprising inserting said liquid sample into a well of the device of claim 1, heating said liquid sample, and heating said opening.

18. A method of heating a liquid sample, said method comprising:
    providing a liquid sample in a container, said container comprising a top surface, and
    heating the top surface of said container, wherein the heat is provided by a heating element above said container, wherein the heating element does not contact the container and is configured to heat the air above the sample, wherein said heating element has an opening therewithin, wherein the opening has a lateral cross-section sized to permit passage of a gripper or liquid dispenser to the container, wherein the heating element heats the opening to a temperature greater than the temperature of the liquid sample, and wherein the opening is configured to allow, throughout the heating process, continuous access to the well by the gripper or liquid dispenser.

19. The method of claim 18, said method further comprises providing a second heating element positioned below or about said container.

20. The method of claim 18, wherein the top of said container contains a slit or a passage.

21. The method of claim 18, further comprising providing a liquid dispenser.

22. The method of claim 21, further comprising dispensing a liquid from said liquid dispenser through said top of said container while said container is positioned below said opening.

23. The method of claim 18, further comprising:
    providing a gripper;
    passing said gripper through said opening;
    gripping the top of said container with said gripper; and
    passing said container through said opening using said gripper.

24. The method of claim 21, further comprising providing a liquid dispenser and a gripper, wherein said liquid dispenser and said gripper are automated.

25. The method of claim 18, wherein said heating element heats said opening to a temperature 10, 20, 30, 40, 50, 75, or 100 degrees centigrade greater than the temperature of said liquid sample.

26. A device for heating a liquid sample, said device comprising:
    (a) a frame comprising at least one well for holding a liquid sample, wherein said frame is on an agitation device;
    (b) a first heating element positioned above the frame, wherein the first heating element does not contact the frame or the sample and is configured to heat the air above the sample;
    (c) an opening positioned within the heating element and above the at least one well, wherein the opening has a lateral cross-section sized to permit passage of a gripper or liquid dispenser to the well, wherein the opening is configured to allow, throughout the device's use, continuous access to the well by the gripper or liquid dispenser; and (d) a second heating element positioned below or about the frame; wherein the first heating element is configured to reach a higher temperature than the second heating element.

* * * * *